(12) United States Patent
Malin (10) Patent No.: US 9,174,790 B2
(45) Date of Patent: Nov. 3, 2015

(54) STORAGE CASSETTE FOR LABORATORY OBJECTS

(71) Applicant: LICONIC AG, Mauren (LI)

(72) Inventor: Cosmas Malin, Mauren (LI)

(73) Assignee: LICONIC AG, Mauren (LI)

( * ) Notice: Subject to any disclaimer, the term of this patent is extended or adjusted under 35 U.S.C. 154(b) by 0 days.

(21) Appl. No.: 14/103,255

(22) Filed: Dec. 11, 2013

(65) Prior Publication Data

US 2014/0190977 A1 Jul. 10, 2014

(30) Foreign Application Priority Data

Dec. 12, 2012 (EP) .................................. 12008284

(51) Int. Cl.
*B65D 81/38* (2006.01)
*F25D 3/10* (2006.01)
*A01N 1/02* (2006.01)
*G01N 35/00* (2006.01)

(52) U.S. Cl.
CPC .............. *B65D 81/38* (2013.01); *A01N 1/0257* (2013.01); *F25D 3/102* (2013.01); *G01N 2035/00435* (2013.01)

(58) Field of Classification Search
CPC ...... B65D 81/38; A01N 1/0257; F25D 3/102; G01N 2035/00435
USPC .......................... 62/45.1, 600, 440, 459, 465; 220/560.04, 560.12, 565, 592.01, 220/592.2, 592.02, 592.09
See application file for complete search history.

(56) References Cited

U.S. PATENT DOCUMENTS

| | | |
|---|---|---|
| 3,272,579 A | 9/1966 | Leonard |
| 3,782,133 A | 1/1974 | Desperier et al. |
| 4,250,266 A | 2/1981 | Wade |
| 4,907,889 A | 3/1990 | Simone |
| 4,969,336 A | 11/1990 | Knippscheer et al. |
| 5,192,506 A | 3/1993 | Kureshy et al. |
| 5,233,844 A | 8/1993 | Knippscheer et al. |
| 5,240,139 A | 8/1993 | Chirnomas |
| 5,345,395 A | 9/1994 | Griner |
| 5,365,980 A * | 11/1994 | deBerardinis ..................... 141/1 |
| 5,435,685 A | 7/1995 | Tsuda et al. |
| 5,628,342 A * | 5/1997 | McNealy et al. ............. 137/587 |

(Continued)

FOREIGN PATENT DOCUMENTS

| | | |
|---|---|---|
| CH | 696 326 A5 | 4/2007 |
| DE | 199 03 958 | 8/2000 |

(Continued)

OTHER PUBLICATIONS

European Search Report conducted in counterpart European Patent Appl. No. EP 120 08 284 (May 22, 2013).

*Primary Examiner* — Robert J Hicks
*Assistant Examiner* — Kareen Thomas
(74) *Attorney, Agent, or Firm* — Greenblum & Bernstein, P.L.C.

(57) ABSTRACT

A storage system (1) has a chamber (3). In the chamber (3), multiple storage tanks (5) are arranged, and a picking and placing device (8) is arranged above these tanks. Carrousels (8) are arranged in the storage tanks. These carrousels are suspended from a top pivot bearing (35) and laterally guided by a bottom pivot bearing (44). The top pivot bearing (35) is located outside the insulation (12) of the storage tanks and is thus protected from extreme temperatures. In the carrousel (18), storage cassettes (20) are arranged which are laterally held by guide elements (31).

17 Claims, 5 Drawing Sheets

(56) References Cited

U.S. PATENT DOCUMENTS

| | | |
|---|---|---|
| 5,735,587 A | 4/1998 | Malin et al. |
| 5,921,102 A | 7/1999 | Vago |
| 6,068,393 A | 5/2000 | Hutchins et al. |
| 6,129,428 A | 10/2000 | Helwig et al. |
| 6,228,636 B1 | 5/2001 | Yahiro et al. |
| 6,694,767 B2 | 2/2004 | Junca et al. |
| 7,314,341 B2 | 1/2008 | Malin |
| 7,527,764 B2 | 5/2009 | Angelantoni et al. |
| 7,544,329 B2 | 6/2009 | Malin |
| 8,677,744 B2 * | 3/2014 | McBride et al. ............ 60/508 |
| 2003/0233842 A1 | 12/2003 | Junca et al. |
| 2005/0260102 A1 | 11/2005 | Angelantoni et al. |
| 2006/0053825 A1 | 3/2006 | Owen et al. |
| 2006/0150659 A1 | 7/2006 | Sidor et al. |
| 2006/0156753 A1 | 7/2006 | Fuhr et al. |
| 2008/0231152 A1 | 9/2008 | Malin |
| 2008/0272674 A1 | 11/2008 | Malin |
| 2010/0183408 A1 | 7/2010 | Malin |
| 2010/0275636 A1 | 11/2010 | Yoshimura et al. |
| 2011/0219788 A1 | 9/2011 | Zimmermann et al. |
| 2012/0060520 A1 | 3/2012 | Collins et al. |
| 2012/0060539 A1 | 3/2012 | Hunt et al. |
| 2012/0060541 A1 | 3/2012 | Hunt et al. |
| 2012/0102983 A1 | 5/2012 | Parmegiani |

FOREIGN PATENT DOCUMENTS

| | | |
|---|---|---|
| DE | 10 2004 008 496 | 7/2005 |
| EP | 0 035 452 | 6/1984 |
| EP | 1 972 874 A2 | 9/2008 |
| JP | 2005-143873 | 6/2005 |
| WO | 97/48309 | 12/1997 |
| WO | 98/43592 | 10/1998 |

* cited by examiner

STORAGE CASSETTE FOR LABORATORY OBJECTS

CROSS-REFERENCE TO RELATED APPLICATIONS

The present application claims priority under 35 U.S.C. §119(a) of European Patent Application No. 12 008 284.7 filed Dec. 12, 2012, the disclosure of which is expressly incorporated by reference herein in its entirety.

FIELD OF THE INVENTION

The invention relates to a storage tank for the low temperature storage of laboratory objects. Low temperature storage thereby refers to a storage at temperatures below 0° C., in particular below −160° C.

BACKGROUND

The storage of laboratory objects at very low temperatures, for example at temperatures below −160° C., typically at −196° C., is very costly and not very accessible to an automation. A storage system for low temperatures is known from EP 1 972 874, but this system is only partly suitable for truly low temperatures.

U.S. 2010/0275636 describes a vacuum-insulated storage tank for laboratory objects with which cryogenic temperatures can be achieved.

U.S. Pat. No. 5,233,844 describes a storage system for cryogenic temperatures in which laboratory objects can be stored in a carrousel inside a thermally insulated storage tank.

SUMMARY OF THE INVENTION

The object is to provide a storage tank of the type mentioned at the outset in which a storage of a large number of laboratory objects is, among other things, also possible at very low temperatures and low cold losses.

This object is attained by the storage tank according to claim 1.

According to this claim, the storage tank contains an interior space and an insulation arranged around the interior space. The interior space is upwardly closed by a cover region. In the cover region, an opening is provided which allows an access to the interior space from outside. A carrousel with storage positions for the laboratory objects is located in the interior space. Furthermore, a top pivot bearing is provided which is arranged above the carrousel and from which the carrousel is pivotably suspended.

Because the carrousel is pivotably suspended, it is possible to forego a heavily weight-bearing pivot bearing at the bottom end of the carrousel. This is advantageous, as it is difficult to provide pivot bearings that are capable of carrying larger weights and withstanding low temperatures.

Advantageously, the top pivot bearing is arranged outside the insulation so that it can in a simple manner be kept at a significantly higher temperature than the interior space of the storage tank. This simplifies the design of the top pivot bearing.

In another advantageous embodiment, the storage tank has a neck section projecting vertically upwards past the cover region. The insulation extends through the cover region and the neck section up to the top end of the neck section. The top pivot bearing is arranged at the top end of the neck section.

Through this design, the duct of the carrousel to the top pivot bearing can be embodied in a relatively long manner so that a cold loss is reduced.

The top pivot bearing is advantageously a swivel joint roller bearing or an axial ball bearing, as such a bearing can also accommodate a relatively large load in an axial direction and is also capable of tolerating slight errors in the alignment. Other advantageous bearing types are separable ball bearings and taper roller bearings because of their axial loadability.

In another advantageous embodiment, the storage objects are stored in storage cassettes, each of which forms a multiple number of storage positions on top of one another. Each storage cassette can be removed as a whole from the storage tank through the opening. The carrousel has a base element which for example can be embodied as a base plate. The storage cassettes rest on the base element. The carrousel has at least one guide element spaced from the base plates, which guide element horizontally guides the storage cassettes resting on the base element but allows a vertical motion of the storage cassettes. Thanks to the guiding element, a tilting of the storage cassettes during the rotation of the carrousel can be easily opposed.

At the bottom end of the carrousel, a bottom pivot bearing can also be provided which limits lateral excursions of the carrousel.

The bottom pivot bearing can be embodied such that no vertical forces bear on it in the normal operation of the storage tank (which is to be understood as meaning that the vertical forces that act on the top pivot bearing are at least ten times larger than the vertical forces that act on the bottom pivot bearing).

However, it is conceivable that the bottom pivot bearing can also accommodate higher forces outside of normal operation, for example during a maintenance or a replacement of the top pivot bearing. In particular, the carrousel can in this case be slightly lowered so that its weight temporarily comes to bear on the bottom pivot bearing.

BRIEF DESCRIPTION OF THE INVENTION

Additional embodiments, advantages and applications of the invention arise from the dependent claims and from the following description based on the drawings. In this matter:

WAYS OF EMBODYING THE INVENTION

Definitions

Terms of the type "top," "bottom," "above," "below," and "horizontal" and "vertical" refer to a system of reference in which the rotation axis of the carrousel of the storage tank is arranged vertically and the base element on which the cassettes rest is located below the cassettes.

Overview:

In the following, a storage system and a storage tank for such a storage system, as well as a storage cassette for the storage tank, are described. However, the storage system is not restricted to the use with the storage tanks or storage cassettes described. The storage tanks are equally as little restricted to the use in the storage system described and with the storage cassettes described, and the storage cassettes can also be used independent of the storage system and the storage tanks.

Figure 1:
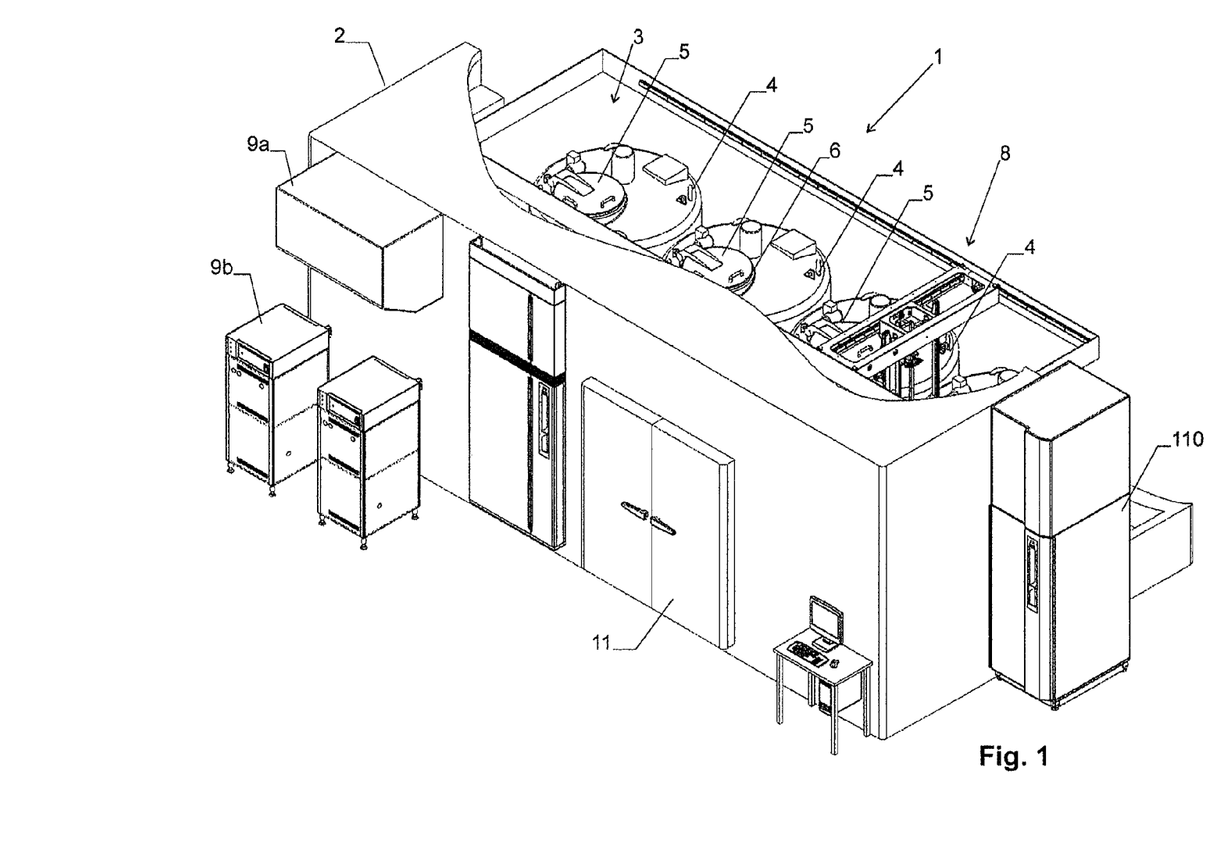
FIG. 1 shows a view of a storage system, wherein the outer walls are only partially illustrated.
Figure 2:
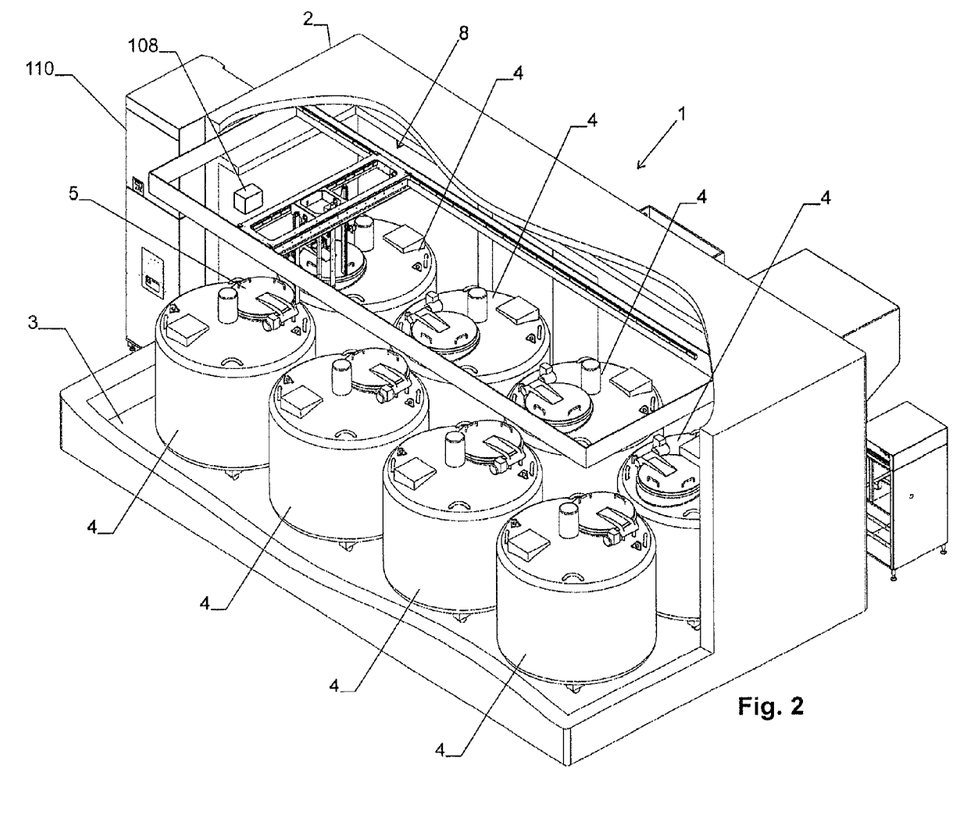
FIG. 2 shows a second view of the storage system from FIG. 1.

Storage System:

FIGS. 1 and 2 show a storage system 1 for the long-term storage of samples at very low temperatures, in particular a storage temperature Ts below −160° C., typically at −196° C. The storage system is embodied to automatically store and remove the samples and to move the samples between different storage positions within the storage system. Systems of this type must meet high demands regarding security of the samples, reliability and energy efficiency.

The samples are for example placed in test tubes, which in turn are arranged in plates. Several of these sample plates are respectively stored on top of one another in a storage cassette.

The storage system has an insulated outer housing 2 which encloses a chamber 3. At least one storage tank 4 is arranged in the chamber 3. Preferably, multiple storage tanks 4 of this type are provided. Each storage tank 4 is preferably embodied as a Dewar vessel and has, in a known manner, an evacuated, mirrored insulation wall which forms a vacuum insulation and has low thermal conduction. In the embodiment shown, the Dewar vessels are closed on all sides, and a lid 5 is respectively provided for accessing their interior space. The lid 5 seals an opening 6 arranged on the surface of the Dewar vessel.

The chamber 3 is preferably embodied as a cooling chamber. The temperature Tc of the chamber 3 is advantageously below 0° C., in particular below −20° C. or −50° C. This lowering of the temperature prevents the formation of ice in the storage tanks 4 or on the samples. The storage temperature Ts in the storage tanks 4 is less than the chamber temperature Tc and is advantageously at the "very low temperatures" mentioned, that is, typically at −196° C.

A cooling of the chamber 3 is, however, not absolutely necessary. The chamber 3 can for example also merely contain a defined atmosphere (for example, dry air or nitrogen atmosphere), or it can be a storage space not specially climate-controlled.

Additionally, a picking and placing device 8 is arranged in the chamber 3. This picking and placing device 8 has respectively one transport device for the storage cassettes, the sample plates and the test tubes. It is moveably arranged above the Dewar vessels 4. As can be seen from FIGS. 1 and 2, exactly one picking and placing device 8 is advantageously provided which services all storage tanks 4.

The storage system furthermore comprises a first cooling apparatus 9a for producing the inside temperature Ti in the chamber 3 as well as a second cooling apparatus 9b for producing the storage temperature Ts in the Dewar vessels 4.

The chamber 3 is accessible via a door 11 which is sufficiently large for the accommodation of the Dewar vessels 4.

Figure 3:
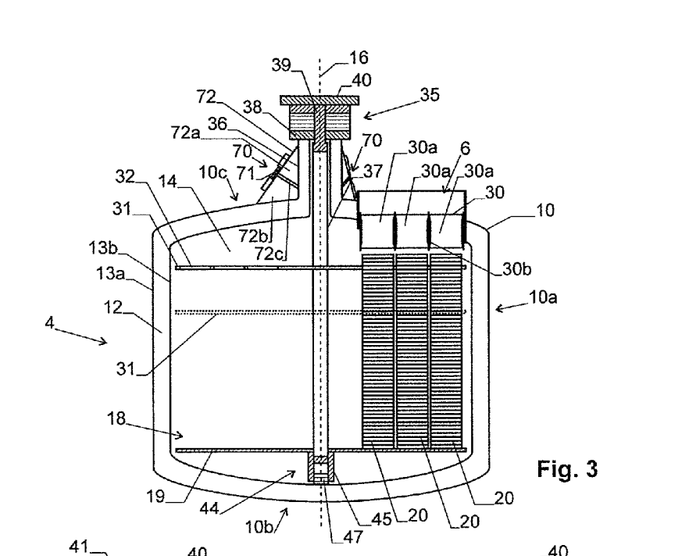
FIG. 3 shows a vertical cross section through a storage tank.
Figure 4:
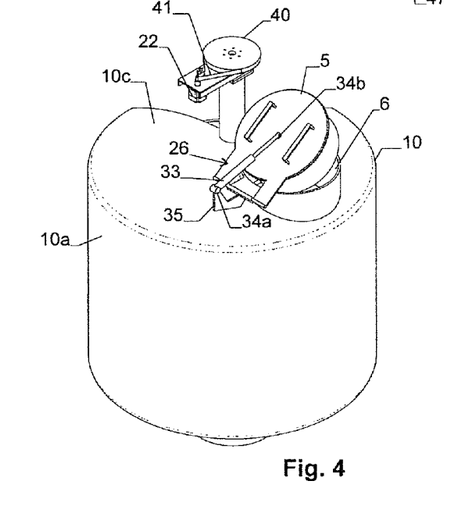
FIG. 4 shows a view of the storage tank according to FIG. 3.
Figure 5:
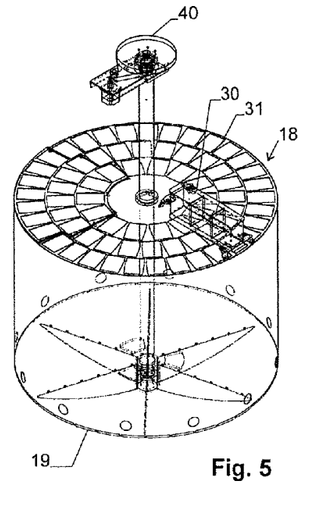
FIG. 5 shows the carrousel of the storage tank according to FIG. 3.

Storage Tanks:

An advantageous embodiment of a storage tank 4 is illustrated in FIGS. 3-5. It has a housing 10 in which the aforementioned vacuum insulation 12 is arranged between an outer wall 13a and an inner wall 13b. The vacuum insulation 12 encloses an interior space 14 which accommodates a carrousel 18 pivotable about a vertical rotation axis 16. The carrousel 18 carries on a base element 19 a plurality of storage cassettes 20, of which three are illustrated in FIG. 3. The storage cassettes 20 are arranged in at least one, preferably in multiple, concentric circles around the rotation axis 16, wherein advantageously multiple storage cassettes stand on each circle.

The housing 10 has an essentially cylindrical outer wall 10a which laterally encloses an interior space 14. The interior space is closed downwardly by an an essentially horizontal base region 10b and upwardly by an essentially horizontal cover region 10c.

A positioning drive 22 (FIG. 4) serves to rotate the carrousel 18 about the rotation axis 16 and bring the carrousel into defined positions.

The door 5 is used to seal the opening 6 can be opened and closed automatically using a door drive 26. The opening 6 is arranged on the top side of the Dewar vessel 4 in the cover region 10c and positioned and sized such that with an open door 5, each storage cassette 20 that was rotated into the region of the opening 6 by the positioning drive 22 can be removed from above. Preferably, the horizontal diameter of the opening 6 is however smaller than the horizontal half diameter of the Dewar vessel 4 so that an excessive cold loss during the opening of the door 5 can be avoided.

A centering element 30 is arranged at the opening 6, in particular in the opening 6. This centering element has for each circle of storage cassettes 20 a vertical passage 30a which laterally guides the storage cassettes during insertion into or removal from the storage tank 4. In other words, the centering element 30 thus has multiple passages 30a that are spaced from the rotation axis 16 of the carrousel 18 at different distances.

The centering element 30 is arranged in a horizontally adjustable manner so that the each passage 30a can be aligned with exactly with the storage positions in the inside of the tank.

As illustrated, the vertical passages 30a are laterally limited by guides 30b with beveled ends so that a misalignment of the storage cassettes can be corrected.

The guides 30b serve as lateral slide bearings for the storage cassettes, and their opposing distance is measured such that the storage cassettes are guided with only little play and large accuracy. The guides 30b have a relatively large height, in particular of at least 5%, advantageously of at least 10%, of the height of the storage cassettes so that they can suitably oppose a tilting of the storage cassettes.

Furthermore, the carrousel 18 has spaced from the base element 19 a guide element 31 that extends essentially horizontally and advantageously has a height significantly smaller than the height of the storage cassettes. It secures the storage cassettes 20 horizontally but permits a vertical motion, that is, it forms horizontal stops so that the cassettes cannot move or tilt horizontally. In the embodiment according to FIGS. 3-5, the guide element 31 is embodied as a plate of the type of a grid which has guide openings 32 at the locations of the storage cassettes 20. The storage cassettes 20 extend through the guide openings 32, and the cross section of the guide openings 32 is slightly larger than the horizontal cross section of the storage cassettes 20.

In order to hold the storage cassettes 20 even better, multiple guide elements 31 can be provided, as indicated dashed in FIG. 3. The guide elements 31 are in this case arranged at different heights.

The guide openings 32 are aligned with the passages 30a of the centering 30.

At the guide openings 32, guide aids in the form of angularly running guide surfaces can be provided, which simplify an insertion of the cassettes. With sufficiently precise positioning and embodiment of the centering element 30, such guide surfaces can however be omitted so that the guide element 31 can be produced in a very simple manner.

As can be seen from FIG. 4, the door drive 26 has a linearly extendible drive element 33, for example in the form of a pneumatic cylinder or hydraulic cylinder. The drive element 33 is connected in a hinged manner to an upwardly protruding pivot bearing 35 of the housing 10 of the storage tank at a first end 34a, and connected in a hinged manner to the door 5 at a second end 34b. The door 5 is likewise attached in a hinged manner to the housing 10 of the storage tank. By retraction or extension of the drive element 33, the door 5 can be opened or closed, respectively.

Figure 6:
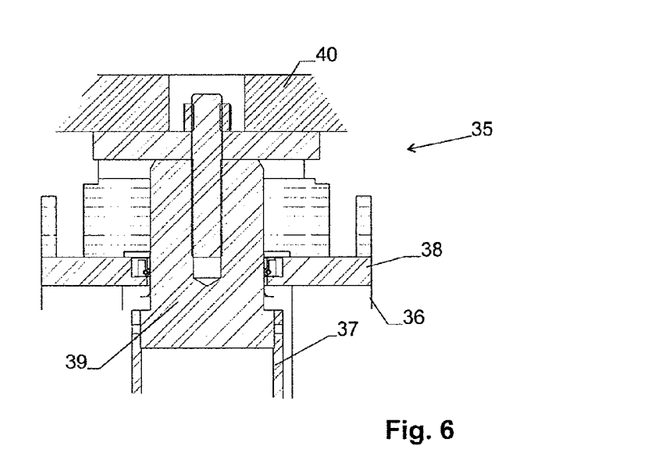
FIG. 6 shows a cross section through the top pivot bearing of the storage tank.
Figure 7:
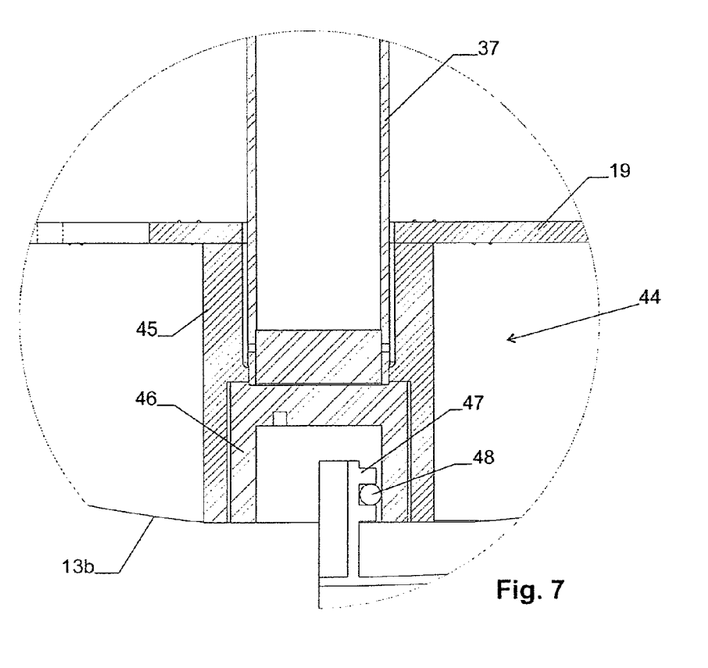
FIG. 7 shows a cross section through the bottom pivot bearing of the storage tank.

The arrangement of the bearings of the carrousel 18 is illustrated in FIGS. 3, 6 and 7.

The carrousel 18 is pivotably suspended in the storage tank 4, that is, its weight is (at least 90%) borne by a top pivot bearing 35 that is located above the carrousel. Preferably, the top pivot bearing 35 is arranged outside the insulation 12 so that it can be operated at a relatively high temperature.

In the embodiment shown, the pivot bearing is located at the top end of a neck section 36 of the storage tank 4. This neck section 36 projects vertically upwards over the cover region 10c, preferably by at least 20 cm. The outer diameter of the neck section 36 is preferably significantly smaller than the outer diameter of the carrousel, in particular less than 10% of the diameter of the carrousel. The insulation 12 extends over the cover area 10c and the neck section up to 36 to the top end of the same so that a thermal bridge is also avoided in the neck section 36.

The carrousel 18 has a drive shaft 37, preferably in the form of a hollow tube for reducing the thermal conduction, which hollow tube extends through the neck section 36 up to the top pivot bearing 35.

The top pivot bearing 35 of the embodiment illustrated rests on the top end 38 of the neck section 36 so that the weight of the carrousel 18 can be suitably transferred to the housing 10.

The top pivot bearing 35 is preferably embodied in a swivel-adjustable manner, that is, it can be swiveled for the adjustment of the rotation axis with respect to the vertical, preferably at least by +/−1°. In this manner, the carrousel can be precisely positioned in the storage tank.

In the embodiment according to FIG. 3, at least three adjustable pull/push elements 70 are provided (not illustrated in FIG. 4) for this purpose with which the neck section 36 can be elastically deflected in at least three different directions. Each pull/push element 70 is capable of applying a horizontal tensile force component and/or an impact force component to the neck section 36, wherein the size of this force component is permanently adjustable.

For example, the pull/push elements 70 have as threaded rods 71 which on the end sides are connected on the one hand to the neck section 36 and on the other hand to the cover region 10c. In the embodiment according to FIG. 3, three pull/push elements 70 of this type are for example provided which are attached to a corresponding number of vertically standing ribs 72. Each rib 72 has a top section 72a, which is attached to the neck section 36, and a bottom section 72b, which is connected to the cover area 10c. The two sections 72a, 72b are separated by a slot 72c which ensures an elastic deformability of the neck section 36.

For the reasons already indicated, the top pivot bearing 35 is preferably a swivel-joint roller bearing, an axial ball bearing, a separable ball bearing or a tapered roller bearing.

A force transmission element 39 is permanently connected to the drive shaft 37 and extends through the top pivot bearing 35 up to a pulley 40 which is driven via a belt 41 by the positioning drive 22 (cf. FIG. 4).

At the bottom end of the carrousel 10, as can be seen from FIGS. 3 and 7, a bottom pivot bearing 44 is provided. For this purpose, a tube section 45 is attached concentrically to the rotation axis 16 at the bottom of the carrousel 18, into the inside of which tube section a roller bearing engages from below. The roller bearing is formed by a ring 46 mounted on the tube section 45, which ring rotates with the carrousel 18, and by a stationary mandrel 47 attached to the base region 10b of the storage tank, between which ring and mandrel rollers or balls 48 run (only the left half of the mandrel 47 and the balls 48 is shown respectively in FIG. 7).

The bottom pivot bearing 44 has the task of restricting lateral excursions of the carrousel 18, but does not need to accommodate any vertically directed weights, so that it can be embodied in a constructively significantly simpler manner than the top pivot bearing 35. Furthermore, the inner wall 13b in the base region 10b does not need to accommodate any large forces, which likewise simplifies the design of the tank.

Figure 8:
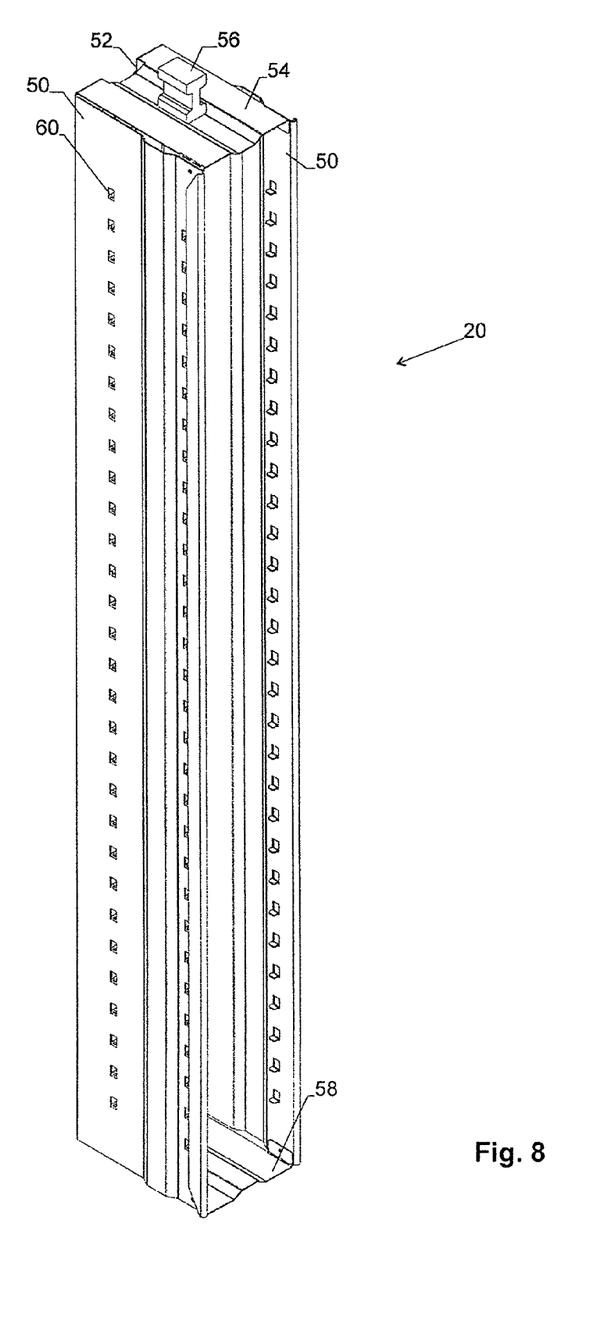
FIG. 8 shows a storage cassette.

Storage Cassettes:

In FIG. 8, an advantageous storage cassette 20 is illustrated. It has two parallel vertical side walls 50 and a vertical rear wall 52 perpendicular thereto. Across from the rear wall 52, the storage cassette 20 is open so that the sample plates or laboratory objects placed in the storage cassette 20 can be accessed. At the top end of the storage cassette 20, a cover part 54 is arranged to which the side walls 50 and the rear wall 52 and a holding element 56 are attached. The holding element 56 is used by the picking and placing device 8 to grasp the cassette. At the bottom end of the storage cassette 20, a base part 58 is arranged to which the side walls 50 and the rear wall 52 are also attached.

The storage cassette 20 forms a plurality of storage positions arranged on top of one another, each of which can accommodate a sample plate or a laboratory object. The storage cassettes are structured such that they ensure a high mechanical precision across a very wide temperature range. Furthermore, they have centering devices and transport devices which enable a high mechanical positioning accuracy and the automatic transport, respectively.

In the embodiment illustrated, each storage position is formed by multiple brackets 60. These brackets protrude inwards from the side walls 50 and the rear wall 52 and form side and rear supports for the sample plates.

Remarks:

The proposed solution allows samples to be stored at very low temperatures in a simple and automated manner. Because the access can occur in an automated manner, very large storage tanks can also be used which would not be suitable for a manual loading due to the large masses needing to be moved and for safety reasons.

While preferred embodiments of the invention are described in the present application, it must be clearly noted that the invention is not limited to these and can also be embodied in a different manner within the scope of the following claims.

The invention claimed is:

1. Storage tank for a low temperature storage of laboratory objects comprising:
   a housing;
   an interior space;
   an insulation arranged around the interior space;
   a cover area which upwardly closes the interior space;
   an opening in the cover area which provides an access to the interior space from outside;
   a carrousel arranged pivotably in the interior space with storage positions for the laboratory objects;
   a top pivot bearing which is located above the carrousel and from which the carrousel is pivotably suspended; and a neck section projecting vertically upwards past the cover area, wherein the insulation extends over the cover area and the neck section up to a top end of the neck section and wherein the top pivot bearing is arranged on the top region of the neck section.

2. Storage tank according to claim 1, wherein the top pivot bearing is arranged outside the insulation.

3. Storage tank according to claim 1, wherein the carrousel has a drive shaft which extends through the neck section to the top pivot bearing.

4. Storage tank according to claim 1, wherein the top pivot bearing rests on a top end of the neck section.

5. Storage tank according to claim 1, wherein the top pivot bearing is a swivel joint roller bearing, an axial ball bearing, a separable ball bearing or a tapered roller bearing.

6. Storage tank according to claim 1, wherein at a bottom end of the carrousel a bottom pivot bearing is provided which limits lateral deflections of the carrousel.

7. Storage tank according to claim 6, wherein no vertical forces bear on the bottom pivot bearing in a normal operation of the storage tank.

8. Storage tank according to claim 1 with a positioning drive for rotating the carrousel.

9. Storage tank according to claim 1, wherein a centering element is arranged at the opening, wherein the centering element has at least one vertical passage for guiding the storage cassettes during the insertion or removal.

10. Storage tank according to claim 1, wherein the top pivot bearing is swivel-adjustable.

11. Storage tank according to claim 1, wherein at least three adjustable pull/push elements are provided at the neck section, with which the neck section can be deflected in at least three different directions.

12. Storage tank for a low temperature storage of laboratory objects comprising:
a housing;
an interior space;
an insulation arranged around the interior space;
a cover area which upwardly closes the interior space;
an opening in the cover area which provides an access to the interior space from outside;
a carrousel arranged pivotably in the interior space with storage positions for the laboratory objects;
a top pivot bearing which is located above the carrousel and from which the carrousel is pivotably suspended; and
a plurality of storage cassettes,
wherein each storage cassette forms a multiple number of storage positions on top of one another, wherein each storage cassette can be removed from the storage tank through the opening, wherein the carrousel has a base element on which the storage cassettes rest, and wherein the carrousel has spaced from the base element at least one guide element which horizontally secures the storage cassettes resting on the base element but permits a vertical motion of the storage cassettes.

13. Storage tank according to claim 12, wherein the guide element is embodied as a plate which has guide openings at locations of the storage cassettes through which the storage cassettes extend.

14. Storage tank according to claim 12, wherein the carrousel has multiple guide elements arranged at different heights.

15. Storage tank for a low temperature storage of laboratory objects comprising:
a housing;
an interior space;
an insulation arranged around the interior space;
a cover area which upwardly closes the interior space;
an opening in the cover area which provides an access to the interior space from outside;
a carrousel arranged pivotably in the interior space with storage positions for the laboratory objects;
a top pivot bearing which is located above the carrousel and from which the carrousel is pivotably suspended; and
a door for sealing the opening and with a door drive for moving the door.

16. Storage tank according to claim 15, the door is arranged in a hinged manner on the housing and wherein the door drive has a linearly extendible drive element which is at a first end hinged and at a second end connected to the door in a hinged manner.

17. Storage tank for a low temperature storage of laboratory objects comprising:
a housing;
an interior space;
an insulation arranged around the interior space;
a cover area which upwardly closes the interior space;
an opening in the cover area which provides an access to the interior space from outside;
a carrousel arranged pivotably in the interior space with storage positions for the laboratory objects; and
a top pivot bearing which is located above the carrousel and from which the carrousel is pivotably suspended,
wherein a centering element is arranged at the opening, wherein the centering element has at least one vertical passage for guiding the storage cassettes during the insertion or removal, and
wherein the centering element has multiple passages spaced at different distances from a pivot axis of the carrousel.

* * * * *